United States Patent
Rostami et al.

(10) Patent No.: US 6,483,935 B1
(45) Date of Patent: Nov. 19, 2002

(54) SYSTEM AND METHOD FOR COUNTING PARTS IN MULTIPLE FIELDS OF VIEW USING MACHINE VISION

(75) Inventors: Fariborz Rostami, Menlo Park, CA (US); Todd O. Dampier, Mountain View, CA (US); Edwin C. Mangalindan, Austin, TX (US)

(73) Assignee: Cognex Corporation, Natick, MA (US)

( * ) Notice: Subject to any disclaimer, the term of this patent is extended or adjusted under 35 U.S.C. 154(b) by 0 days.

(21) Appl. No.: 09/430,107

(22) Filed: Oct. 29, 1999

(51) Int. Cl.[7] .................................................. G06K 9/00
(52) U.S. Cl. ......................................... 382/141; 382/194
(58) Field of Search ................................. 382/141, 142, 382/143, 192, 194, 104, 133, 134; 209/509, 551; 348/86; 198/958; 340/933, 934, 937

(56) References Cited

U.S. PATENT DOCUMENTS

| | | | |
|---|---|---|---|
| 4,962,538 A | * 10/1990 | Eppler et al. | 250/222.2 |
| 5,040,056 A | * 8/1991 | Sager et al. | 348/88 |
| 5,298,697 A | * 3/1994 | Suzuki et al. | 187/380 |
| 5,317,645 A | * 5/1994 | Perozek et al. | 209/522 |
| 5,581,625 A | * 12/1996 | Connell | 348/139 |
| 6,215,892 B1 | * 4/2001 | Douglass et al. | 382/128 |

FOREIGN PATENT DOCUMENTS

| | | |
|---|---|---|
| GB | 2226130 A | 6/1990 |
| GB | 2309078 A | 7/1997 |

* cited by examiner

Primary Examiner—Jon Chang
(74) Attorney, Agent, or Firm—William Loginov

(57) ABSTRACT

A system and method for counting objects or parts on a continuously moving conveyor, or other elongated surface, provides a camera and associated machine vision system that acquire/capture and analyze multiple, successive fields of view taken within an area of interest defined by the system. Each of the fields of view includes flanking right and left overlap zones with respect to adjacent fields of view. The overlap zones are defined to be at least as wide as the maximum width of a part being counted. The captured fields of view are stored within the system and analyzed in succession based upon a set of rules. These rules determine whether or not a particular part within the subject field of view is to be counted. More specifically, the rules are applied within the overlap zones for each field of view to determine whether or not to count the part. Certain refinements to basic rules are employed to establish uncertainty regions within the overlapping zones to account for possible errors in tracking objects between fields of view.

22 Claims, 6 Drawing Sheets

SYSTEM AND METHOD FOR COUNTING PARTS IN MULTIPLE FIELDS OF VIEW USING MACHINE VISION

FIELD OF THE INVENTION

This invention relates to machine vision systems and more particularly to systems for counting objects on a moving conveyor belt or other elongated surface.

BACKGROUND OF THE INVENTION

During mass production processes, conveyor belts are used extensively. Manufactured objects such as cans, pill bottles, small parts, and the like, are transported between production processes on a variety of conveyor belts. Often, conveyor belts are wider than the minimum width of a given object and, thus, objects may be transported down a conveyor belt in a somewhat staggered random arrangement with objects often dispersed along the conveyor belt in a variety of spacing and orientations with respect to each other.

Machine vision systems are capable of counting distinct shapes on a surface using a variety of advanced techniques including pattern recognition. In general, one or more images of the objects within a field of view are captured and analyzed, producing an object count. However, most machine vision systems rely on one camera (or at most a few cameras) with a limited field of view for acquiring images of objects. A conveyor is, by definition, a constantly changing picture within any field of view. When the conveyor belt carries a somewhat random spacing and arrangement of objects, it is very difficult to accurately count these objects, especially when images are captured at a relatively high rate. The combination of unpredictable arrangement of parts and relative speed of movement along the conveyor belt makes it hard to track these objects between image captures, even if the underlying objects are fixed to a conveyor belt by means of a vacuum belt system. In other words, it is possible for objects to pass out of the field of view between image captures (and be missed entirely), or to be double-counted in consecutive image captures It is, therefore, an object of this invention to provide a system and method for accurately tracking and counting objects as they move down a continuously moving conveyor belt at a normal process speed. The placement of the objects on the belt should not affect counting accuracy. This system and method should further enable counting of stationary objects on an elongated surface covering several camera fields of view.

SUMMARY OF THE INVENTION

This invention overcomes the disadvantages of the prior art by providing a system and method for more accurately counting objects or parts on an elongated surface (a continuous moving conveyor belt, herein) having relative movement with respect to a camera with a limited field of view, thereby requiring multiple fields of view. The system acquires a plurality of images from the belt, representing a plurality of "fields of view" as consecutive portions of the belt (with associated parts thereon) pass below the camera's area of interest. Each of the fields of view includes flanking right and left overlap zones with respect to adjacent fields of view. The overlap zones are defined to be at least as wide as the maximum width of a part being counted. The captured fields of view are stored within the system and analyzed in succession based upon a set of rules. These rules determine whether or not a particular part within the subject field of view is to be counted. More specifically, the rules are applied within the overlap zones for each field of view to determine whether or not to count the part. In a preferred embodiment, in general the basic counting rules (subject to refinements to be described below) for each field of view a on belt moving in an "upstream" (left, herein) to "downstream" (right, herein) direction are as follows:

1. If a part resides partially or fully in the upstream overlap zone, then do not count the part.

2. If a part resides partially or fully in the center section, then count the part.

3. If a part resides fully in the downstream overlap zone, then count the part.

4. If a part resides partially in the downstream overlap zone, then do not count the part.

According to one embodiment, the parts are typically held against the belt during movement using, for example, a vacuum belt. The inspection station includes a CCD camera, or equivalent, having a triggered electronic shutter or triggered strobe flash that sets a limited periodic interval for viewing the parts in each field of view. The trigger can be switched by an encoder operatively connected to the belt and arranged to activate the shutter or strobe periodically as the belt moves a predetermined incremental distance.

In order to account for inherent errors within the conveyor and imaging system, the overlap zones can further define uncertainty regions that are generally twice the maximum acceptable error in width. Based upon the position of the assigned "origin" of each part image, within a field of view, with respect to the uncertainty regions, a part is either considered for counting/non-counting, and/or assigned to a holdover set that includes the part's location and whether it was counted. If a match to the part is found in the previous holdover set, then the part is counted if it was not already counted.

BRIEF DESCRIPTION OF THE DRAWINGS

The foregoing and other objects and advantages of the invention will become more clear with reference to the following detailed description as illustrated by the drawings in which.

DETAILED DESCRIPTION

Figure 1:
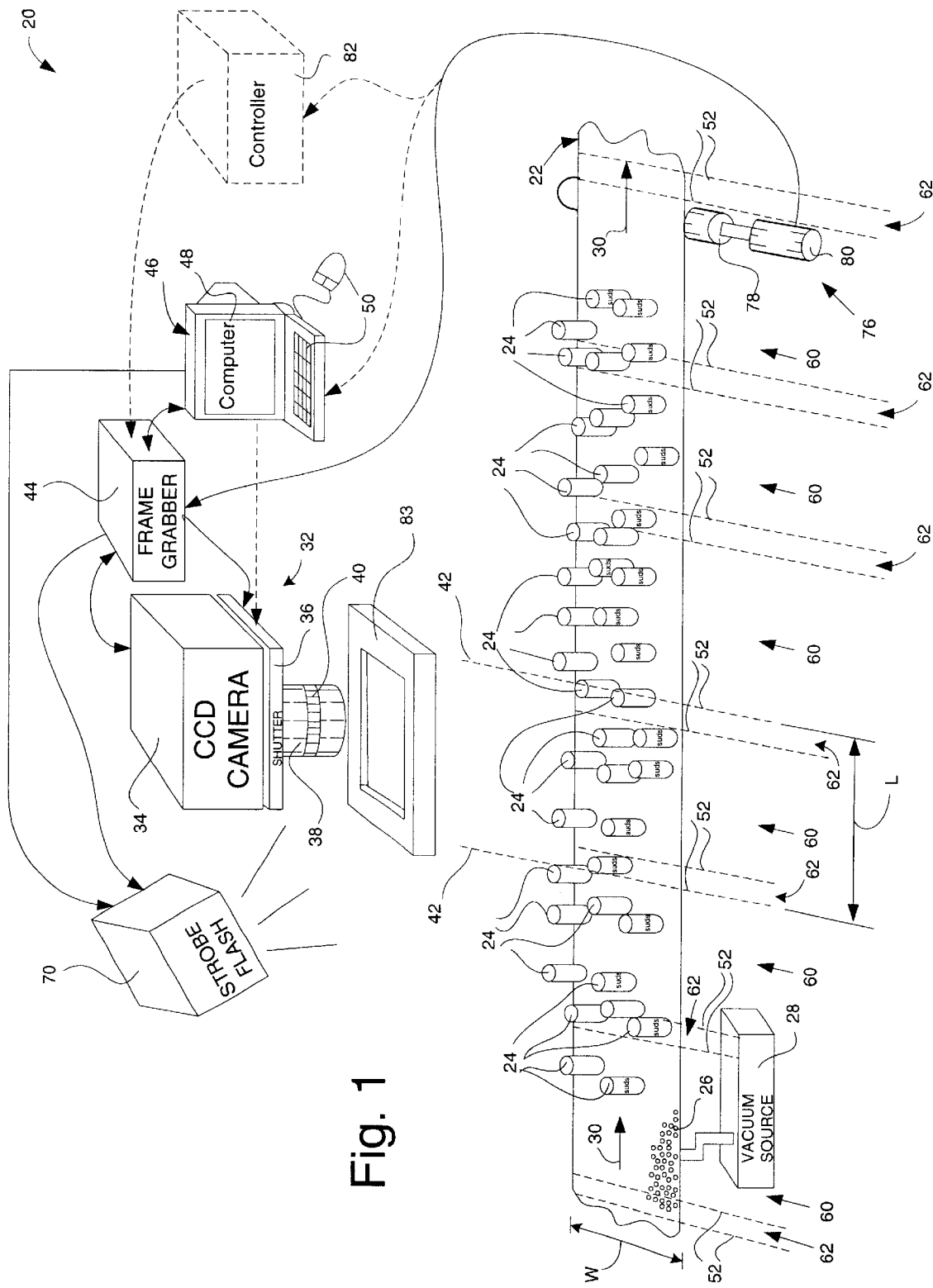
FIG. 1 is a somewhat schematic perspective view of a system for counting parts on a continuously moving conveyor belt according to this invention.

FIG. 1 shows a system 20 for counting objects or parts carried on a continuously moving conveyor belt 22. The objects or parts 24 are a stream of upright parts (cans in this example) disposed relatively randomly along the belt 22 in the illustrated example. The terms "object" and "part" will be used generally herein to describe any set of items moving along a conveyor or, disposed along an elongated surface that requires multiple fields of view to be fully acquired by an imaging camera. In this particular example, the width W of the belt is approximately eighteen inches while the diameter of each part (can) has a footprint on the belt of approximately two inches, enabling a significant number of parts to be placed aside one another in relatively skewed orientations therebetween.

The belt can include a series of ports 26 or similar perforations along its surface that are in communication with a vacuum source 28 the resulting draw on the ports 26 generates a vacuum attraction for the parts 24. In this manner, they are maintained in their relative positions on the belt 22. Their source and destination are adapted to deposit the parts and remove the parts, respectively, without regard to their random placement on the belt. For the purposes of this description, the belt moves in the direction of the arrow 30 (e.g. left to right). However, the belt can move in the opposite direction or upwardly and downwardly.

Suspended over the belt 22 is an imaging camera assembly 32. The assembly 32 can include a base member 34 having a color or gray scale Charge Coupled Device (CCD) element of conventional design. The camera can include an integral or separate electronic shutter assembly 36, which will be described further below. A lens 38 is mounted to the assembly 32. It can include manual or automatic focus and aperture control, exemplified by the ring 40. The lens is positioned with respect to the conveyor belt 22 so that a length L of the belt is viewable, thereby defining the camera's area of interest (dashed lines 42). This area is typically less than the maximum field of view of the camera, and can be defined electronically using machine vision software (described further below).

The camera 34 is electronically coupled to a video processor including a frame grabber 44 that is conventional in design. The video processor 44 is, in turn, coupled to a computer system 46 including a display 48 and user controls (keyboard and mouse) 50. The computer system 46 includes software for pattern recognition and machine vision. This software can be conventional according to preferred embodiment. Such software can include various packages that utilize normalized correlation techniques, boundary search or, more advanced packages such as PatMax available from Cognex, Corp. of Natick, Mass.

Software such as PatMax has internal capabilities to differentiate between sections of a viewed image based upon predefined boundaries within the image. These boundaries can be determined based upon the overall number of image pixels in a given section or upon other criteria. More particularly, the software can determine the center or "origin" of a given part image. This is a point on the part that is used to track its location with respect to the overall field of view in which the part image is present. The origin is assigned upon initial analysis of the given part image and is maintained for that part image in succeeding fields of view.

In this embodiment, the computer system software is adapted to establish fields of view at succeeding time intervals as the belt moves. In other words, each time the belt moves a predetermined distance, the fixed camera snaps an image of the area of interest, which remains fixed over a given location with respect to the moving belt. The various boundaries of respective fields of view are denoted in the figures by dashed lines 52. Each field of view is defined by its own respective central section or zone 60 and a flanking pair of left and right overlapping sections or zones 62. Each field of view, in essence, shares its overlapping sections with adjacent fields of view. An overlapping section or zone in fields of view is formed specifically when an image of the area of interest is acquired by the camera at a time in which the conveyor belt has not moved completely beyond the previous acquired image (e.g. the previous field of view). The width of previous, imaged field of view still within the present field of view (the left or "upstream" side of the previous field herein) defines the overlapping section.

Note that each central section 60 is somewhat arbitrary in width. It is typically defined by the area that the camera can accurately cover and that the computer machine vision system can reliably analyze. In general, the central section 60 is sufficiently sized to accommodate several parts in a lengthwise direction according to this embodiment. The relationship between central and overlapping sections and their function will be described in detail below. In summary, the computer machine vision system is adapted to identify parts in each field of view and compare those identified with those in adjacent field of view applying rules (described below) to count or not count parts falling within these overlapping sections.

Figure 2:
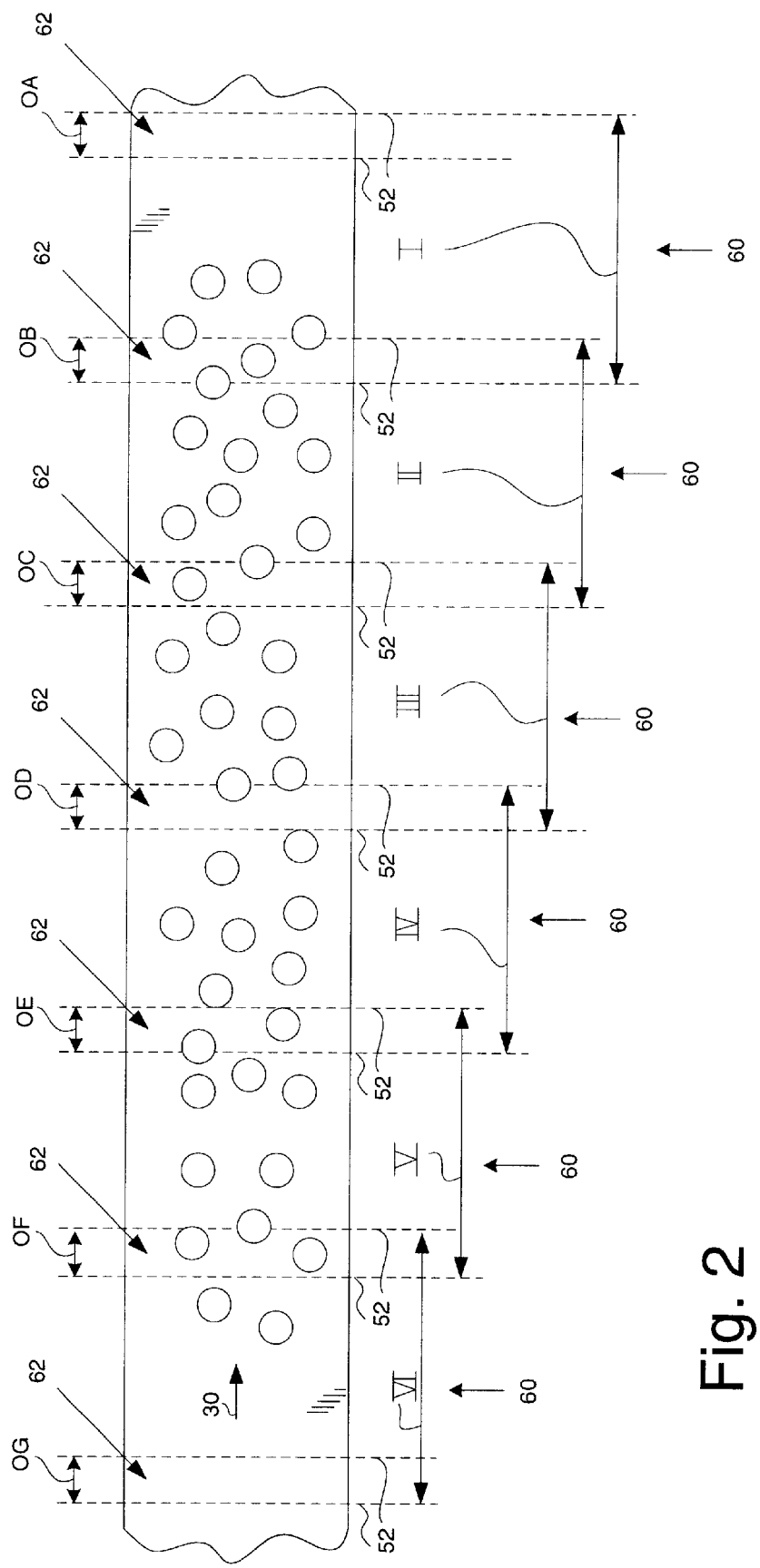
FIG. 2 is a plan view of the conveyor belt of FIG. 1 further defining a plurality of fields of view therealong according to this invention.

With further reference to FIG. 2, fields of view I, II, III, IV, V and VI are defined in succession as each passes beneath the cameras area of interest (this area being particularly defined by dashed lines 42 in FIG. 1). Field of view I includes overlapping (right and left) sections OA and OB. Field of view II includes overlapping sections OB and OC. Field of view III includes overlapping sections OC and OD. Field of view IV includes overlapping sections OD and OE. Field of view V includes overlapping sections OE and OF. And, finally, field of view VI includes overlapping sections OF and OG. The width of the overlapping region is typically defined to be at least as large as (and generally larger than) the largest dimension of an imaged object moving on the conveyor belt plus any other errors expected to be encountered during the movement of the belt (to be described in further detail below). In this example, a two-inch diameter part would have an overlap region of at least two inches so that the part fully lies within an overlap region under certain circumstances.

Again, the computer system is adapted to acquire images of the fields of view I–VI in succession at periodic time intervals. These time intervals can be at least several times per second, dependant upon the relative speed of the conveyor. If the conveyor is moving quickly, then a higher frequency of image acquisition is employed, while a slower moving conveyor belt may entail a lower frequency of image acquisition.

According to one embodiment, an electronic shutter 36, described above, is triggered at preset intervals of distance to acquire an instantaneous view of the moving parts beneath the camera's area of interest. The shutter can be an actual physical shutter device, or the electronic equivalent operating to momentarily poll for an image from the CCD camera. Likewise, the "shutter" can be appropriate image processing software downstream of the CCD camera according to an alternate embodiment (such as a frame grabber function).

According to an alternate embodiment, a strobe flash 70 can be employed. The strobe flash is triggered at the desired frequency to flash bright illuminating light on the area of interest for brief durations. Where a strobe flash 70 is used, the inspection area of the conveyor should be maintained in relative darkness using, for example, an overlying cover or equivalent types of blinds so that an image is not acquired by the computer system between strobe flashes.

The frequency of triggering of the strobe flash 70, shutter 36, or any internal frame grabber is generally controlled by the relative movement of the conveyor belt. To this end, the belt is operatively interconnected with a measuring assembly. The measuring assembly according to this embodiment includes a wheel 78 and associated encoder 80. As a predetermined distance of belt moves along, the wheel 78 rotates, causing an analog or digital signal (distance-related pulses for example) to be generated by the attached encoder 80 mechanism. Any acceptable technique for measuring relative movement of the belt is contemplated. For example, the measuring assembly can be a mark reader that reads periodic optical marks on the belt as they pass by a fixed sensor or a internal circuitry within the conveyor drive motor that reports relative movement (a stepper motor for example). Therefore, the term's "encoder" and/or "measuring assembly" should be taken broadly to include any acceptable belt-movement-measuring device.

The encoder 80 is interconnected with either the computer system 46 or the frame grabber 44 or a separate controller 82. Typically the strobe and and/or shutter is controlled by the frame grabber so to synchronize these elements. In addition the system typically includes a high-frequency illuminator shown here as a rectangular element 83. In each case, the encoder signal is translated into an appropriate movement distance measurement according to a preprogrammed scalar. Each time a predetermined movement distance occurs, with respect to the preceding triggering event (e.g. the preceding field of view), the next field of view is acquired. The distance between triggering events is chosen so that the desired overlap distance between fields of view is maintained. To accomplish this, the steady state triggering distance is generally set to equal the sum of the central section distance plus the distance of one overlapping section. The images acquired in each field of view are stored for counting analysis either on a cumulative basis or a shifting basis. The counting process is now described in further detail.

Each time an image is acquired by the system, the machine vision software, using conventional pattern recognition techniques, identifies the parts present within each respective field of view I–VI. This includes both the central sections 60 and respective left and right overlapping sections. The identification and location can be based upon the specific location of the "origin" of the each part within the field of view or more broadly, based upon all or part of the part's acquired outline. Having recognized the individual parts within each field of view, and having determined whether these parts lie within the central section 60 or within overlapping sections of each field of view, the system then applies a set of rules to determine the total part count for the particular field of view.

In general the basic counting rules (subject to refinements to be described below) for each field of view a on belt moving in an "upstream" (left, herein) to "downstream" (right, herein) direction are as follows:

1. If a part resides partially or fully in the upstream overlap zone, then do not count the part.
2. If a part resides partially or fully in the center section, then count the part.
3. If a part resides fully in the downstream overlap zone, then count the part.
4. If a part resides partially in the downstream overlap zone, then do not count the part.

The foregoing rules operate in an idealized environment where fields of view are accurately triggered based upon belt movement and virtually no part movement with respect to the belt occurs. In such an environment, the rules adequately insure that parts passing through the camera's area of interest are counted in their entirety, and that no part is counted twice. Now an exemplary application of the ideal rules based upon the arrangement of parts shown in FIG. 2 is discussed.

Figure 3:
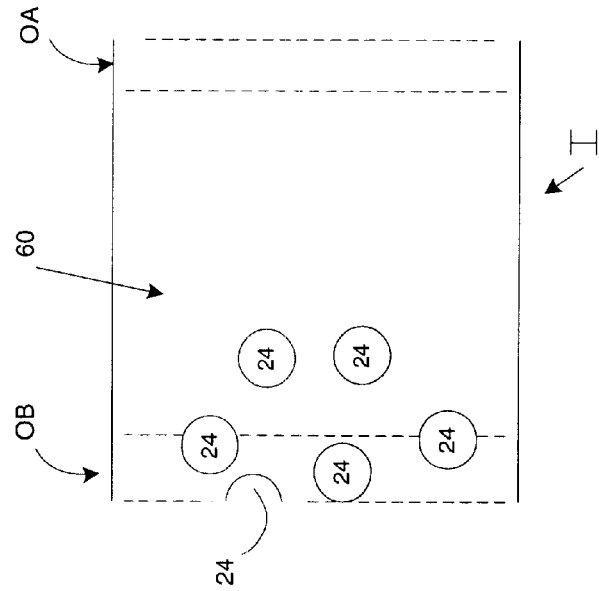

As shown in FIG. 3, the parts 24 have the following distribution in field of view I:

2 partially in left overlap zone (OB)—0 count;

1 fully in left overlap zone (OB)—0 count; and 4 partially or fully in central section—4 count.

Total for field of view I—4 count.

Figure 4:
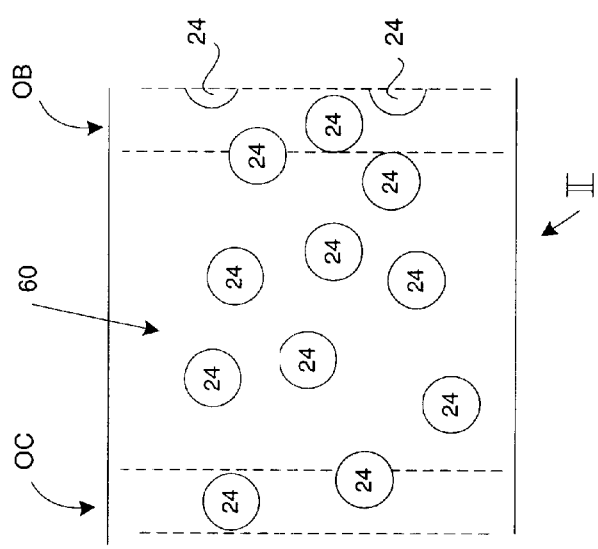

As shown in FIG. 4, the parts 24 have the following distribution in field of view II:

3 partially outside right overlap zone (OB)—0 count;

1 fully in right overlap zone (OB)—1 count;

9 partially or fully in the central section—9 count;

1 partially in left overlap zone (OC)—0 count; and 1 fully in left overlap zone (OC)—0 count.

Total for field of view II—10 count.

Figure 5:
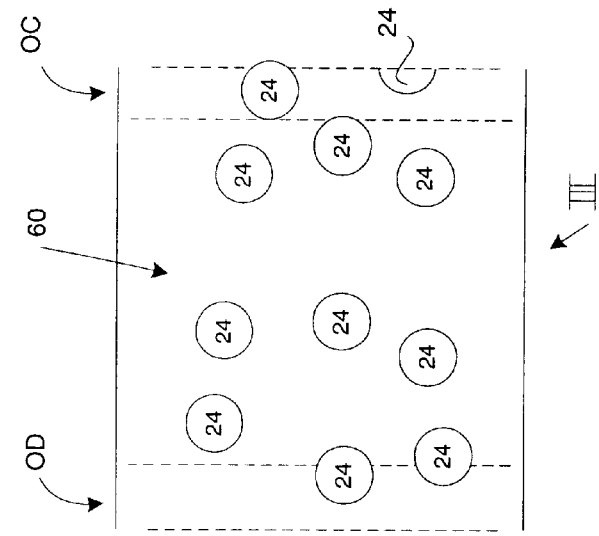
FIGS. 3–8 are respective plan views of individual fields of view taken along the conveyor belt of FIG. 2 a plurality of successive image-capture time intervals.

As shown in FIG. 5, the parts 24 have the following distribution in field of view 1 partially in right overlap zone (OC)—0 count;

1 fully in right overlap zone (OC)—1 count;

9 partially or fully in the central section—9 count;

2 partially in the left overlap zone (OD)—0 count; and 1 fully in left overlap zone (OD)—0 count.

Total for field of view III—10 count.

Figure 6:
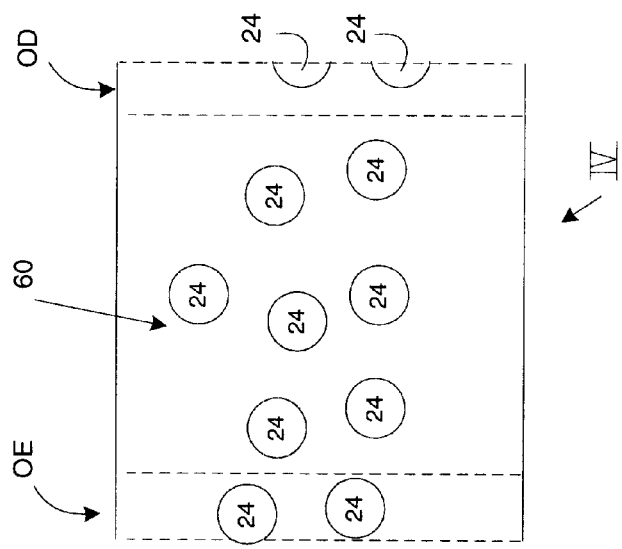

As shown in FIG. 6, the parts 24 have the following distribution in field of view IV:

2 partially in right overlap zone (OD)—0 count;

7 partially or fully in the central section—7 count;

1 fully in left overlap zone (OE)—0 count; and 1 partially in left overlap zone (OE)—0 count.

Total for field of view IV—7 count.

Figure 7:
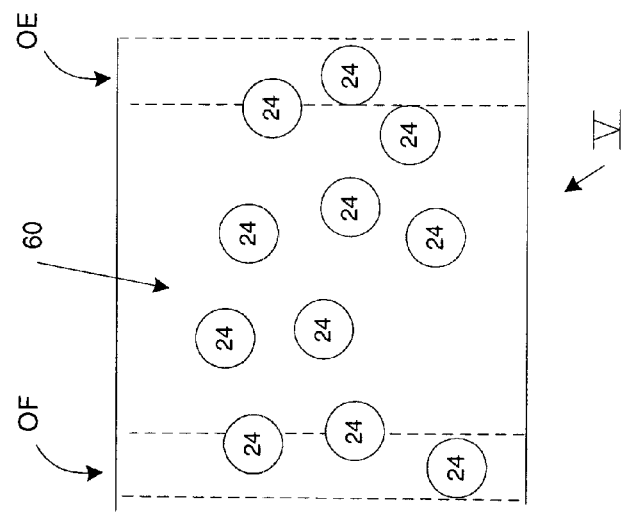

As shown in FIG. 7, the parts 24 have the following distribution in field of view V:

1 fully in right overlap zone (OE)—1 count;

1 partially in right overlap zone (OE)—0 count;

8 partially or fully in the central section—8 count;

1 fully in left overlap zone (OF)—0 count; and 2 partially in left overlap zone (OF)—0 count.

Total for field of view V—9 count.

Figure 8:
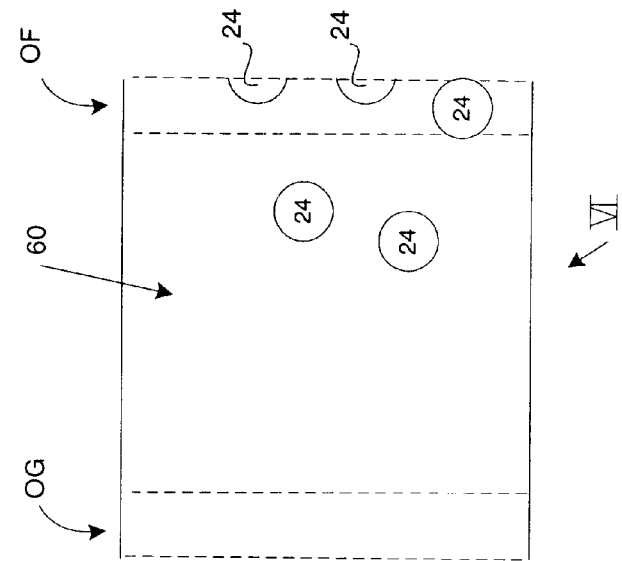

And finally, as shown in FIG. 8, the parts 24 have the following distribution in field of view VI:

2 partially in right overlap zone (OF)—0 count;

1 fully in right overlap zone (OF)—1 count; and 2 partially or fully in the central section—2 count.

Total for field of view VI—3 count.

This results in a total count in the analyzed fields of view I–VI of 43 parts, which accurately reflects the total number of parts shown in the continuous belt view of FIG. 2.

Again, the ideal rule works well where part position can be accurately controlled and images can be taken at precise intervals with respect to the belt movement. However, there are certain factors that may cause an actual count, based upon the ideal rules, to err. These factors include certain inherent resolution limitations and internal inconsistencies and measurement drift in the encoder, which may cause fields of view to be triggered at imprecise spacing. Another cause of errors may be inaccuracy in locating parts (in an x-y-coordinate system) within the machine vision system. Parts may also be subject to distortion that may cause origins to be misjudged. Finally, and most significantly, the parts may be subject to jostling and movement as the transit the conveyor belt between fields of view. Each of these conditions, or all together, may be present in an actual conveyor to varying degrees, causing the system to count either too many or too few parts.

Figure 9:
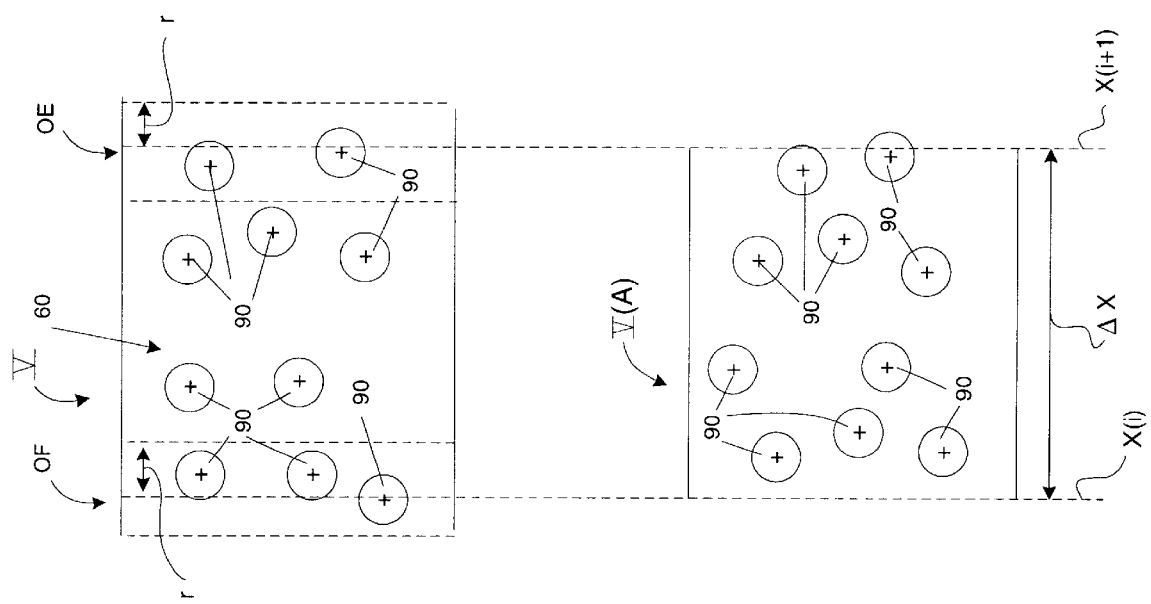
FIG. 9 is a plan view of an exemplary field of view showing a redefinition of field of view taking into account uncertainty about part positions.

Accordingly, the ideal rules can be modified to account for predictable errors. Reference is first made to FIG. 9 that shows, by way of example, field of view V. As noted above, individual parts are identified by the machine vision system generally by their origins (circle centers) 90. In other words, the position of this origin determines the location of the part within the field of view. Such locations are typically defined based upon x-axis and y-axis coordinates within the overall machine-vision-defined field of view. Under ideal circumstances, the belt moves between line X(i) and line X(i+1). These lines are taken through the center of overlapping regions OE and OF of field of view V in the illustrated example. The amount of movement between fields of view can be defined as $\Delta X$ in other word, ideally, the movement between fields of view is recorded half way down the middle of each adjacent overlapping region.

More specifically, these lines are taken at a distance of r from the right-hand side of overlapping regions OE and OF of field of view V in the illustrated example, where r is half the width (half the diameter, the radius, in the illustrated circular example) of a part. The ideal amount of movement between fields of view can be defined as $\Delta X$. In other words, ideally, the movement between fields of view is recorded halfway down the middle of each adjacent overlapping region. The actual "counting region" is therefore theoretically defined by the illustrated modified view V(A). This counting region is where a part is counted if its origin's x coordinate satisfies the equation $X(i) \leq x < X(i+1)$, where $\Delta X = X(i+1) - X(i)$, and in which i is an arbitrary number indication a given field of view and (i+1) is the succeeding (next) field of view.

Figure 10:
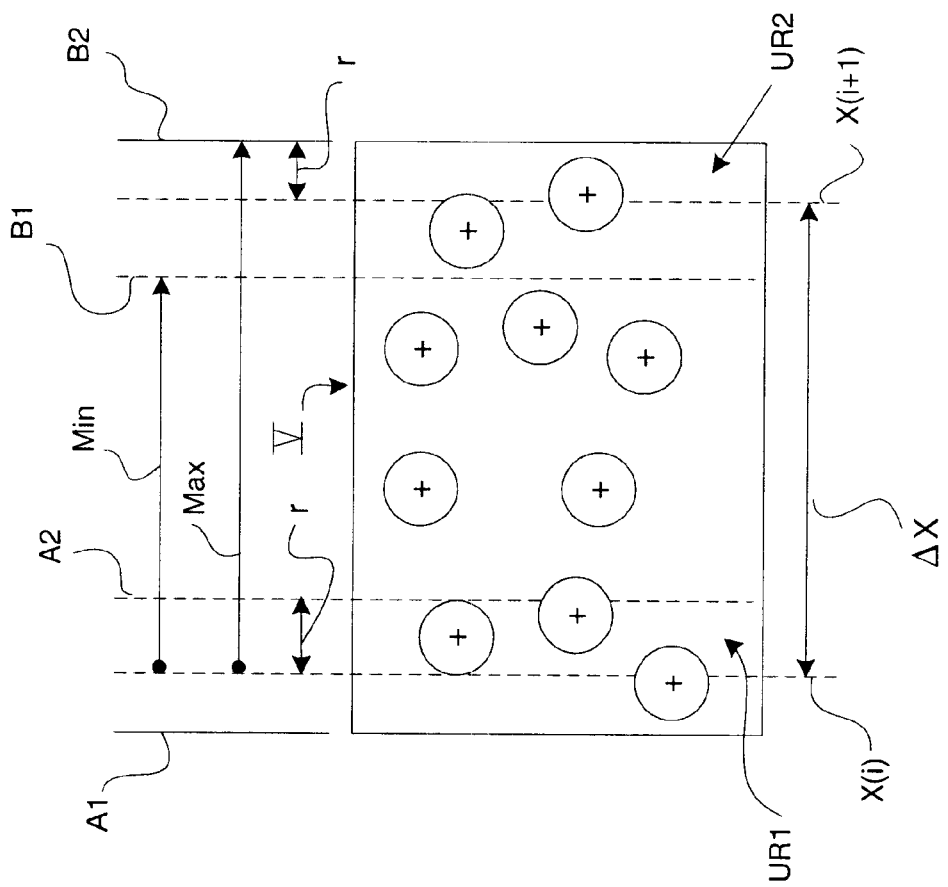
FIG. 10 is a plan view defining minimum and maximum movement errors for parts.

Let e be defined as the maximum amount of error that a part's motion between successive fields of view can experience. That is to say, if a part's origin is located at X(i) in field of view i, then its location in field of view i+1 can be at most $X(i) + \Delta X + e$, and must be at least $X(i) + \Delta X - e$. In other words, the largest expected range of movement between fields of view for any part is $\Delta X \pm e$. With reference now to FIG. 10, it thus can be assumed that the minimum part motion (MIN) between fields of view would involve the translation of the part from the line X(i) to a line at $X(i) + \Delta X - e$, which is, by the definition of $\Delta X$, identical to the line at $X(i+1) - e$. This line is labelled B1 in FIG. 10. Likewise, the maximum part motion (MAX) between fields of view would involve the translation of the part from the line X(i) to a line $X(i+1) + e$. This line is labelled B2 in FIG. 10.

Similarly, if we observe that a part's origin is at X(i+1) in field of view i+1, then we may assume that its position in the preceding field of view i was at least $X(i+1) - \Delta X - e$, and at most $X(i+1) - \Delta X + e$. These are shown as A1 and A2 in FIG. 10.

Based on this reasoning, uncertainty regions UR1 and UR2, respectively, are defined outside the left and right boundaries of the counting region V(A). These regions are bounded by the pair of lines A1 and A2 and the pair of lines B1 and B2, respectively. These regions are, in essence, an area where the identification of a part may or may not result in that part appearing in the next field of view or having appeared in the previous field of view.

Based upon the existence of such uncertainty regions the rules can be modified to account for them. While these rules are generally applicable to any surface in which fields of view move from upstream to downstream, for simplicity, the description will address the moving belt of this example, in which the left uncertainty region is located "upstream" and the right uncertainty region is located "downstream." The terms are interchangeable. Based upon this convention, the following specific outcomes are observed:

1. Parts lying to the left of the left uncertainty region UR1 will fall within the counting region in the next field of view;
2. Parts within the left uncertainty region may or may not be inside the counting region in the next field of view;
3. Parts to the right of the left uncertainty region will definitely be beyond the counting region in the next field of view;
4. Parts to the left of the right uncertainty region had not yet entered the counting region in the previous field of view;
5. Parts within the right uncertainty region may or may not have been inside the counting region in the previous field of view; and
6. Parts to the right of the right uncertainty region were definitely within the counting region in the previous field of view.

Accordingly, given the above observations, the rules are modified so that:

1. If a part is in the counting region of a given field of view, and not in either uncertainty region, simply count it.
2. If a part is in the left uncertainty region then count the part if its origin has an x-coordinate value x>X(i), meaning that it is only partially in the left uncertainty region and its origin is in the counting region.
3. For parts in the left uncertainty region define a "holdover set" that stores the part's coordinates, and whether or not it was counted in the present field of view. (In an ideal movement, the holdover set will be identical to the next frame's right uncertainty region.)
4. If the part is in the right uncertainty region, search for a match (by comparing parts' x-y coordinates in the present and preceding fields) with a part in the previous holdover set, and if the part is found then count it in the present filed of view if it was not counted in the previous field of view.
5. If a part in the right uncertainty region does not match any part in the previous holdover set, then:
    A. If the part is in the left half of the right uncertainty region (where its coordinate x<X(i+1)) then count it, since it cannot have moved less than $\Delta X - e$.
    B. If the part is in the right half of the right uncertainty region (where coordinate x>X(i+1) then do not count the part, since it cannot have moved more than $\Delta X + e$.

The foregoing rules further insure that all parts are counted accurately, so long as the upper bound of any possible errors in movement or detection of parts between fields of view is properly quantified.

The foregoing has been a detailed description of a preferred embodiment of the invention. Various modifications and additions can be made without departing from the spit and scope of the invention. For example, the techniques described herein can be used to analyze a variety of objects, all of the same shape, or having different shapes/sizes, so long as the machine vision system can properly identify and track the various objects. Objects can move along a continuous conveyor/moving surface that is linear, curved or even a circular carousel. It is desired primarily that appropriate fields of view be acquired as movement of the conveyor occurs. In addition, the techniques described herein can be used to analyze fixed or moveable structures on a fixed surface such as a long plate. In this case, the structure is moved under an inspection camera, or the camera itself, is moved to acquire portions of a fixed surface at a certain rate of speed, thereby allowing fields of view to be acquired according to the techniques described herein. In such an instance, the camera transport mechanism would include an appropriate encoder for tracking relative movement to thereby trigger acquisition of images in successive fields of view. It is contemplated mainly that there be "relative movement" between the camera area of interest and the surface. Such "relative movement" can also comprise the pivotal movement of a fixed camera and even changes in a wide-angle image to acquire different fields of view within an overall large field for a completely fixed camera. While the techniques described herein relate primarily to counting, other data can be acquired during the inspection process by machine vision or visual observation. Accordingly, this description is meant to be taken only be way of example and not to otherwise limit the scope of the invention.

What is claimed is:

1. A system for counting objects on an elongated surface comprising:
    a camera that defines an area of interest with respect to an elongated direction of the surface, the camera and the surface being in relative movement with respect to each other in an upstream-to-downstream direction;
    a vision system for identifying locations of objects occurring within the area of interest within a predetermined interval;
    a trigger mechanism that operates at predetermined times to enable the vision system to acquire an image within the area of interest each time the surface moves a predetermined distance along the elongated direction, the trigger mechanism being constructed and arranged so that each acquired image overlaps an adjacent acquired image by a predetermined overlap distance along the elongated direction, thereby defining, in each area of interest, a central section, an upstream overlapping section upstream of the central section, and a downstream overlapping section downstream of the central section; and
    a counter constructed and arranged to count (a) objects identified that are located at least partially in the central section and (b) objects identified that are located fully within only one of either the upstream overlapping section and the downstream overlapping section in the area of interest for each acquired image.

2. The system as set forth in claim 1 wherein the surface is a moving conveyor and is operatively connected to a movement measuring device that provides a signal based upon the movement for the predetermined distance of the surface, and further comprising a controller responsive to the measuring device that operates the trigger mechanism at the predetermined times each time the predetermined movement of the surface is signaled.

3. The system as set forth in claim 2 further comprising a shutter assembly operatively connected to the camera constructed and arranged to selectively acquire an image at the predetermined times in which the trigger mechanism operates.

4. The system as set forth in claim 2 further comprising a strobe flash responsive to the controller, constructed and arranged to illuminate the area of interest to thereby acquire an image by the camera at the predetermined times in which the trigger mechanism operates.

5. The system as set forth in that claim 1 wherein the counter is constructed and arranged to define an upstream uncertainty region associated overlaid upon the upstream overlapping region and a downstream uncertainty region overlaid upon the downstream overlapping region, based upon a predetermined range of expected erroneous movement of the objects in the elongation direction between each acquired image in the area of interest.

6. The system as set forth in claim 5 wherein each of the upstream uncertainty region and the downstream uncertainty region is defined as a distance in the elongated direction that is a difference between a maximum expected erroneous movement of the objects and a minimum expected erroneous movement of the objects and wherein each of the upstream uncertainty region and the downstream uncertainty region is at a respective outer upstream boundary and outer downstream boundary of the area of interest and each of the upstream uncertainty region and downstream uncertainty region has a width from the respective outer upstream boundary and outer downstream boundary to a respective inner upstream boundary and inner downstream boundary, in the elongated direction, of at least one half the difference.

7. The system as set forth in claim 6 wherein the counter is further constructed and arranged (A) to count only the objects located fully in the uncertainty region and (B) to define a counting region between each of the inner upstream boundary of the upstream uncertainty region and the inner downstream boundary of the downstream uncertainty region, and further including:
    (a) means for counting the objects located in the upstream uncertainty region when the objects therein are located only partially in the left uncertainty region and that have respective predetermined origin points thereof located in the counting region;
    (b) means for defining a holdover set including the objects having the respective predetermined origin points thereof located in the upstream uncertainty region, the holdover set including, for each of the objects located therein, a respective location thereof, and determining whether or not each of the objects included in the holdover set is respectively counted in association with the acquired image;
    (c) means for counting the objects in the downstream uncertainty region if (I) the holdover set for a previous acquired image includes the objects and (II) the included objects are not counted in association with the previous acquired image.

8. The system as set forth in claim 1 wherein the counter is further constructed and arranged to count only the objects located fully in the downstream overlapping section and including means for selectively counting the objects located in the downstream uncertainty region of the acquired image if the objects are located in an upstream uncertainty region of a directly previous acquired image and not counted in association with the previous acquired image.

9. A method for counting objects on an elongated surface comprising:
    defining, with a camera, an area of interest with respect to an elongated direction of the surface, the camera and the surface being in relative movement with respect to each other in an upstream to downstream direction;
    identifying, with a vision system, locations of objects occurring within the area of interest within a predetermined interval;
    triggering the acquiring of an image by the vision system within the area of interest each time the surface moves a predetermined distance along the elongated direction, wherein each acquired image overlaps an adjacent acquired image by a predetermined overlap distance along the elongated direction, thereby defining, in each area of interest, a central section, an upstream overlapping section upstream of the central section, and a downstream overlapping section downstream of the central section; and counting (a) objects identified that are located at least partially in the central section and (b) objects identified that are located fully within only one of either the upstream overlapping section and the downstream overlapping section in the area of interest for each acquired image.

10. The method as set forth in claim 9 further comprising moving the surface and generating, based upon movement of the surface for the predetermined distance at the predetermined times, a signal, and wherein the triggering step occurs in response to the signal.

11. The method as set forth in claim 10 further comprising operating a shutter assembly, operatively connected to the camera, to selectively acquire an image at the predetermined times based upon the triggering step.

12. The method as set forth in claim 10 further comprising illuminating the area of interest with a flash to thereby acquire an image by the camera at the predetermined times in response to the signal.

13. The method as set forth in that claim 9 wherein the counting step includes defining an upstream uncertainty region overlaid on the upstream overlapping region and a down stream uncertainty region overlaid on the downstream overlapping region, based upon a predetermined range of expected erroneous movement of the objects in the elongated direction between each acquired image in the area of interest.

14. The method as set forth in claim 13 further comprising defining each of the upstream uncertainty region and the downstream uncertainty region as a distance in the elongated direction that is a difference between a maximum expected erroneous movement of the objects and a minimum expected erroneous movement of the objects and so that each of the upstream uncertainty region and the downstream uncertainty region is at a respective outer upstream boundary and outer downstream boundary of the area of interest and each of the upstream uncertainty region and downstream uncertainty region has a width from the respective outer upstream boundary and outer downstream boundary to a respective inner upstream boundary and inner downstream boundary, in the elongated direction, of at least one half the difference.

15. The method as set forth in claim 14 wherein the counting step includes (A) counting only the objects located fully in the downstream overlapping section and (B) defining a counting region between each of the inner upstream boundary of the upstream uncertainty region and the inner downstream boundary of the downstream uncertainty region, and further including:

(a) counting the objects located in the upstream uncertainty region when the objects therein are located only partially in the upstream uncertainty region and that have respective predetermined origin points thereof located in the counting region;

(b) defining a holdover set including the objects having the respective predetermined origin points thereof located in the upstream uncertainty region, the holdover set including, for each of the objects located therein, a respective location thereof, and determining whether or not each of the objects included in the holdover set is respectively counted in association with the acquired image;

(c) counting the objects in the downstream uncertainty region if (I) the holdover set for a previous acquired image includes the objects and (II) the included objects are not counted in association with the previous acquired image.

16. The method as set forth in claim 9 wherein the counting step comprises counting only the objects located fully in the downstream overlapping section and including selectively counting the objects located in the downstream uncertainty region of the acquired image if the objects are located in an upstream uncertainty region of a directly previous acquired image and not counted in association with the previous acquired image.

17. A method for counting objects experiencing relative movement with respect to an area of interest in an upstream-to-downstream direction, wherein images of the objects are acquired at respective predetermined time intervals based upon the relative movement, the method comprising:

(A) acquiring images in succession within the area of interest, wherein each of the images includes an downstream overlapping region with respect to a directly preceding of the images and an upstream overlapping region with respect to a directly succeeding of the images;

(B) counting all the objects that have a respective origin point located between each of the downstream overlapping region and the upstream overlapping region for each of the images;

(C) counting all the objects that have the respective origin point thereof located in only one of either the upstream overlapping region and the downstream overlapping region for each of the images.

18. The method as set forth in claim 17 further comprising defining an upstream uncertainty region overlaid on the the upstream overlapping region and a downstream uncertainty region overlaid on the downstream overlapping region, based upon a predetermined range of expected erroneous movement of the objects in the upstream-to downstream direction between each acquired image in the area of interest.

19. The method as set forth in claim 18 further comprising defining each of the upstream uncertainty region and the downstream uncertainty region as a distance in the elongated direction that is a difference between a maximum expected erroneous movement of the objects and a minimum expected erroneous movement of the objects and so that each of the upstream uncertainty region and the downstream uncertainty region is at a respective outer upstream and outer downstream boundary of the area of interest and each of the upstream uncertainty region and downstream uncertainty region has a width from the respective outer upstream boundary and outer downstream boundary to a respective inner upstream boundary and inner downstream boundary, in the upstream-to-downstream direction, of at least one half the difference.

20. The method as set forth in claim 19 wherein the counting step (B) includes counting only the objects located fully in the downstream uncertsainty region and defining a counting region between each of the inner upstream boundary of the upstream uncertainty region and the inner downstream boundary of the downstream uncertainty region, and further including:

(a) counting the objects located in the upstream uncertainty region when the objects therein are located only partially in the upstream uncertainty region and that have respective predetermined origin points thereof located in the counting region;

(b) defining a holdover set including the objects having the respective predetermined origin points thereof located in the upstream uncertainty region, the holdover set including, for each of the objects located therein, a respective location thereof, and determining whether or not each of the objects included in the holdover set is respectively counted in association with the acquired image;

(c) counting the objects in the downstream uncertainty region if (I) the holdover set for a previous acquired image includes the objects and (II) the included objects are not counted in association with the previous acquired image.

21. A method for counting objects experiencing relative movement with respect to an area of interest in an upstream-to-downstream direction, wherein images of the objects are acquired at respective predetermined time intervals based upon the relative movement, the method comprising:

(A) acquiring images in succession within the area of interest, wherein each of the images includes a downstream overlapping region with respect to a directly preceding of the images and an upstream overlapping region with respect to a directly succeeding of the images;

(B) defining each of an upstream uncertainty region and a downstream uncertainty region as a distance in the elongated direction that is a difference between a maximum expected erroneous movement of the objects and a minimum expected erroneous movement of the objects, the upstream uncertainty region being bounded by a respective outer upstream boundary and downstream uncertainty region being bounded by an adjacent outer downstream boundary, each of the upstream uncertainty region and the downstream uncertainty region having a width from the respective outer upstream boundary and outer downstream boundary to a respective inner upstream boundary and inner downstream boundary, in the elongated direction, of at least one half the difference;

(C) counting each of the objects having a respective origin point located between the upstream uncertainty region and the downstream uncertainty region;

(D) defining, for each of the objects having a respective origin point located in the upstream uncertainty region, a holdover set that stores the objects respective location, and assigning to the holdover set a respective count indicator for each of the objects that is counted in the upstream uncertainty region; and (E) counting each of the objects having a respective origin point located in the downstream uncertainty region that correspond to respective objects in the holdover set for the directly preceding of the images for which a count indicator is absent.

22. The method as set forth in claim 21 wherein the difference comprises approximately one-half a width of one of the objects.

* * * * *